(12) United States Patent
Yamaguchi et al.

(10) Patent No.: US 7,416,702 B2
(45) Date of Patent: Aug. 26, 2008

(54) HYDROGEN SENSOR AND PROCESS FOR PRODUCTION THEREOF

(75) Inventors: Akira Yamaguchi, Iwate (JP); Katsuhiko Fukui, Iwate (JP)

(73) Assignee: Mikuni Corporation, Tokyo, Chiyoda-Ku (JP)

( * ) Notice: Subject to any disclaimer, the term of this patent is extended or adjusted under 35 U.S.C. 154(b) by 591 days.

(21) Appl. No.: 11/058,013

(22) Filed: Feb. 15, 2005

(65) Prior Publication Data
US 2005/0189223 A1 Sep. 1, 2005

(30) Foreign Application Priority Data
Feb. 27, 2004 (JP) ............................. 2004-055185

(51) Int. Cl.
*G01N 30/96* (2006.01)
*G01N 7/00* (2006.01)
*B05D 7/00* (2006.01)
*C23C 14/00* (2006.01)
*G01N 33/00* (2006.01)
*G01N 31/22* (2006.01)

(52) U.S. Cl. .................... 422/88; 422/56; 422/57; 73/23.2; 73/31.05; 436/144; 436/147; 427/402; 427/419.1; 427/419.4; 204/192.1

(58) Field of Classification Search ............... 73/31.05; 436/144
See application file for complete search history.

(56) References Cited

U.S. PATENT DOCUMENTS

| 6,006,582 A * | 12/1999 | Bhandari et al. ........... 73/31.06 |
| 6,463,789 B2 * | 10/2002 | Moos et al. ................ 73/31.05 |
| 2002/0017126 A1 | 2/2002 | DiMeo, Jr. et al. ......... 73/31.05 |
| 2003/0153088 A1 | 8/2003 | DiMeo, Jr. et al. .......... 436/113 |

FOREIGN PATENT DOCUMENTS

| WO | WO 00/43772 A1 | 7/2000 |
| WO | WO 02/082045 A2 | 10/2002 |

* cited by examiner

*Primary Examiner*—Jill Warden
*Assistant Examiner*—Neil Turk
(74) *Attorney, Agent, or Firm*—Christa Hidebrand; Norris McLaughlin & Marcus, PA (57) ABSTRACT

According to the present invention there is disclosed a hydrogen sensor comprising
  a substrate,
  a rare earth metal film formed on the substrate, and
  a protective film formed on the rare earth metal film,
wherein the protective film comprises a ceramic material and hydrogen-permeable metal particles dispersed in the ceramic material.

12 Claims, 10 Drawing Sheets

Fig.6 Flow of production of hydrogen sensor

High concentration side (for concentration control)

HYDROGEN SENSOR AND PROCESS FOR PRODUCTION THEREOF

TECHNICAL FIELD

The present invention relates to a hydrogen sensor and a process for producing the hydrogen sensor. More particularly, the present invention relates to a hydrogen sensor used for detection of hydrogen gas of relatively low concentration leaking from various devices such as fuel cell for automobile, fuel cell for household use, and the like, or a hydrogen sensor suitably used for applications such as control of hydrogen gas of relatively high concentration in a device handling hydrogen gas, as well as to a process for producing such a hydrogen sensor.

BACKGROUND ART

The demand for hydrogen is predicted to increase sharply in various industrial fields. With such a background, development of a hydrogen sensor used for detection of leakage of hydrogen gas or for measurement of hydrogen gas concentration is in progress.

With respect to the sensor for detection of hydrogen gas, various proposals have been made heretofore. For example, there was proposed a sensor using, as a hydrogen detection element, a thin film of a rare earth metal such as yttrium (Y), lanthanum (La) or the like (the claim of Japanese National Publication of International Patent Application No. 2002-535651).

In this proposal, the change in physical properties of rare earth metal which appears when the rare earth metal is exposed to hydrogen, is utilized for detection of hydrogen. In this sensor, in order to prevent the harmful influence which the rare earth metal receives from the non-hydrogen gas components present together with hydrogen, such as nitrogen, oxygen, ammonia, hydrocarbons and the like, the surface of the rare earth metal film is covered with a protective film composed of, for example, palladium (Pa), platinum (Pt) or an alloy thereof, all having hydrogen permeability.

However, hydrogen-permeable metals such as Pd, Pt and the like expand or contract whenever they absorb or release hydrogen. This expansion and contraction causes mechanical stress, which deteriorates the hydrogen-permeable metal with the lapse of time and generates cracks, etc. Therefore, a hydrogen sensor using a hydrogen-permeable metal as a protective film is inferior in durability.

Further, the hydrogen-permeable metals such as Pd, Pt and the like tend to diffuse into a rare earth metal such as yttrium (Y), lanthanum (La) or the like. As this diffusion proceeds, the hydrogen detectability of the rare earth metal decreases with the lapse of time. Therefore, a hydrogen sensor using a hydrogen-permeable metal as a protective film has a problem in durability.

Furthermore, since Pd or Pt is a very expensive metal, a hydrogen sensor using such a metal as a protective film incurs a high production cost.

The above-mentioned hydrogen sensor has other problems; that is, the structure is complicated and, since the sensor can detect only a low concentration of hydrogen, the application thereof may be limited to warning of hydrogen leakage. Therefore, the hydrogen sensor is unusable in an application of quantitatively determining a high concentration of hydrogen for control of the concentration of the hydrogen gas or in an application of immediately stopping a system in an emergency case.

Thus, development of a hydrogen sensor of good durability and low cost is desired strongly.

DISCLOSURE OF THE INVENTION

The present invention has been made in view of the above situation and aims at providing a hydrogen sensor which can suppress the harmful influence which the effective component of the sensor receives from non-hydrogen gas components or the deterioration of the sensor caused by hydrogen and further can detect a high concentration of hydrogen gas, as well as a process for producing such a hydrogen sensor.

The present invention is as follows.

[1] A hydrogen sensor comprising
 a substrate,
 a rare earth metal film formed on the substrate, and
 a protective film formed on the rare earth metal film,
  wherein the protective film comprises a ceramic material and hydrogen-permeable metal particles dispersed in the ceramic material.

[2] The hydrogen sensor according to [1], wherein the rare earth metal film has a thickness of 5 to 1,000 nm and the protective film has a thickness of 5 to 40 nm.

[3] The hydrogen sensor according to [1], wherein a content of the hydrogen-permeable metal particles in the protective film is 30 to 70% by mass.

[4] The hydrogen sensor according to [1], wherein the rare earth metal film is constituted by at least one kind selected from the group consisting of yttrium, cerium and lanthanum.

[5] The hydrogen sensor according to [1], wherein the hydrogen-permeable metal particles are composed of at least one kind selected from the group consisting of palladium (Pd), platinum (Pt), niobium (Nb), vanadium (V) and tantalum (Ta).

[6] The hydrogen sensor according to [1], wherein the ceramic material is composed of at least one kind selected from the group consisting of $AlNx_1$, $AlOx_2$, $SiNx_3$ and $SiOx_4$ wherein $0.5 \leq x_1 \leq 1$, $0.8 \leq x_2 \leq 1.5$, $0.7 \leq x_3 \leq 1.3$ and $1 \leq x_4 \leq 2$.

[7] The hydrogen sensor according to [1], wherein the protective film is constituted by same or different two or more layers.

[8] The hydrogen sensor according to [1], wherein the substrate is a glass sheet or a ceramic sheet.

[9] The hydrogen sensor according to [1], wherein the substrate is provided with a heater.

[10] The hydrogen sensor according to [9], wherein the heater is a resistor film formed on one side of the substrate, which is made of platinum, ruthenium oxide or a silver-palladium alloy.

[11] The hydrogen sensor according to [1], wherein the rare earth metal film has a thickness of 5 to 100 nm and which is used for detection of hydrogen concentration of 1% by volume or less.

[12] The hydrogen sensor according to [1], wherein the rare earth metal film has a thickness of 100 to 1,000 nm and which is used for detection of hydrogen concentration of 1% by volume or more.

[13] A process for producing a hydrogen sensor according to [1], which comprises forming, on one side of a substrate, a rare earth metal film by vapor-phase growth or sputtering and then forming, on the rare earth metal film, a protective film by simultaneous vapor-phase growth or sputtering of a hydrogen-permeable metal and a ceramic material.

The protective film of the hydrogen sensor of the present invention comprises a ceramic material and hydrogen-permeable metal particles dispersed in the ceramic material substantially uniformly. The hydrogen-permeable metal particles show volume expansion and contraction when absorbing and releasing hydrogen. This volume expansion and contraction is accepted by the ceramic material of high rigidity and the resulting mechanical stress is undertaken by the ceramic material. As a result, the deterioration of the hydrogen-permeable metal due to the reaction with hydrogen is low, allowing the protective film to possess increased durability.

The protective film used in the hydrogen sensor of the present invention is superior in hydrogen gas permeability. This protective film, however, has no permeability to gases other than hydrogen, for example, nitrogen and oxygen. The protective film has selective permeability to hydrogen gas in mixed gas and feeds hydrogen gas to the rare earth metal film. Thus, the present hydrogen sensor has high selectivity to hydrogen gas.

In the hydrogen sensor of the present invention, since the protective film has no permeability to non-hydrogen gases such as nitrogen, oxygen, hydrocarbons and the like, the reduction in capability of sensor (rare earth metal film) due to non-hydrogen gases is prevented.

Further, in the hydrogen sensor of the present invention, since the contact area of the hydrogen-permeable metal in the protective film with the rare earth metal constituting the rare earth metal film is small, the diffusion of the hydrogen-permeable metal into the rare earth metal can be made small. Thereby, the reduction in the hydrogen detectability of the rare earth metal film with the lapse of time, caused by the diffusion can be prevented.

In the hydrogen sensor of the present invention, since the deterioration of the protective film, caused by the absorption and release of hydrogen gas can be prevented, the thickness of the protective film can be made extremely small. Consequently, hydrogen permeation is easy and there can be secured a hydrogen permeability about equal to that of a conventional thick protective film composed of Pd alone. Further, since the thickness of the protective film is small, the use amount of expensive hydrogen-permeable metal can be made small, making it possible to produce a hydrogen sensor of low cost.

In these figures, 1 is a hydrogen sensor; 2 is a substrate; 3 is a rare earth metal film; 5 is a protective film; 5a is a first protective film; 7 is a second protective film; 13 is hydrogen-permeable metal particles; 13a is hydrogen-permeable metal particles in the first protective film; 15 is a ceramic matrix; 15a is a ceramic matrix in the first protective film; 17 is hydrogen-permeable metal particles in the second protective film; 19 is a ceramic matrix in the second protective film; t3 is the thickness of the rare earth metal film; t5 is the thickness of the protective film; t5a is the thickness of the first protective film; t7 is the thickness of the second protective film; 31 is a substrate; 32a and 32b are each an element electrode; 33 is a heater; 34a and 34b are each a heater electrode; 35a and 35b are each a wire; 36 is a rare earth metal film; 37 is a protective film; 41 is a filter; 42 is a cap; 43 is a pin; 44 is a plate; 45 is a grommet; 46 is a cord; and 47 is a connector.

BEST MODE FOR CARRYING OUT THE PRESENT INVENTION

The present invention is described in more detail below with referring to the accompanying drawings.

Figure 1:
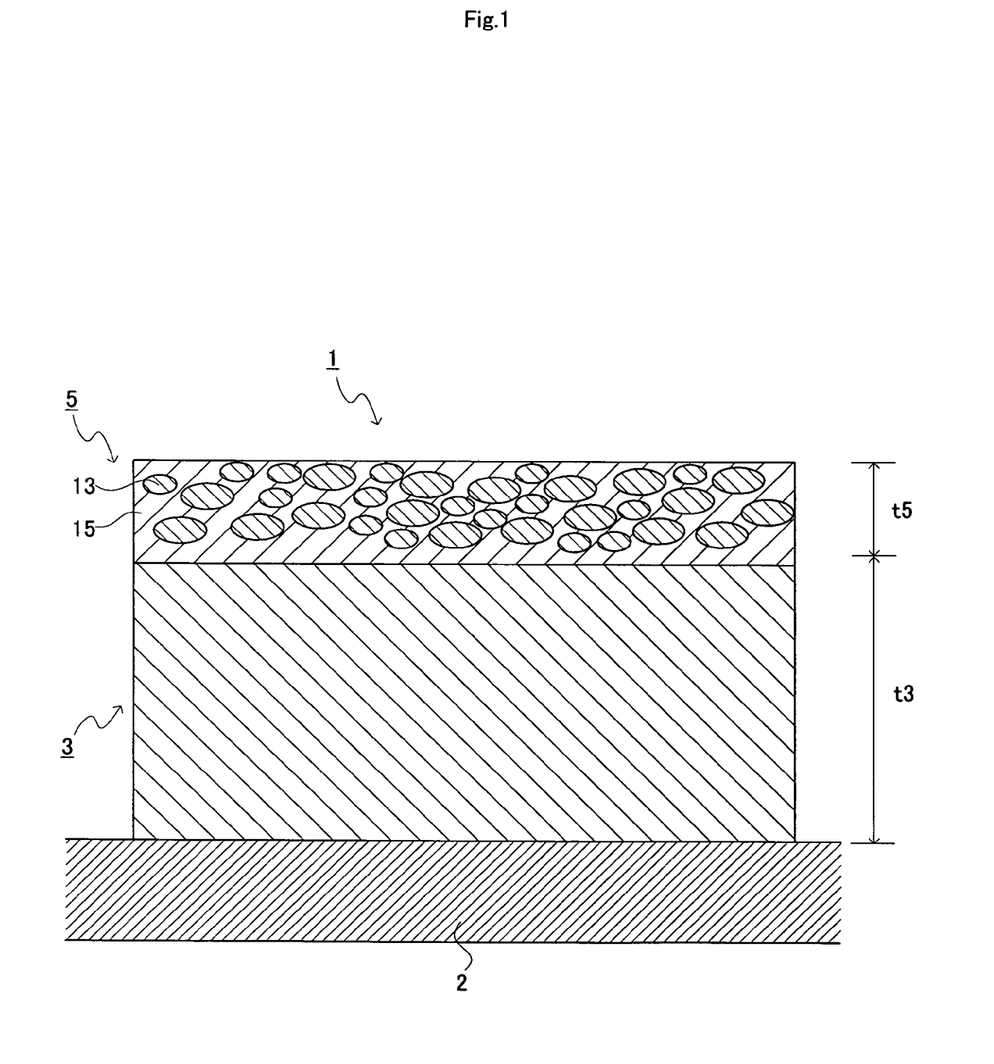
FIG. 1 is a sectional view of an example of the hydrogen sensor of the present invention.

FIG. 1 is a conceptual drawing showing an example of the hydrogen sensor of the present invention. In FIG. 1, 1 is a hydrogen sensor and 2 is a substrate. A rare earth metal film 3 is formed on the substrate 2, and a protective film 5 is formed on the rare earth metal film 3. The protective film 5 comprises a ceramic material 15 (which is a matrix) and a large number of hydrogen-permeable metal particles 13 dispersed in the matrix substantially uniformly. The diameters of the hydrogen-permeable metal particles 13 are 1 to 10 nm, preferably 2 to 6 nm and are smaller than the thickness t5 of the protective film 5. In FIG. 1, t3 is the thickness of the rare earth metal film 3.

Figure 2:
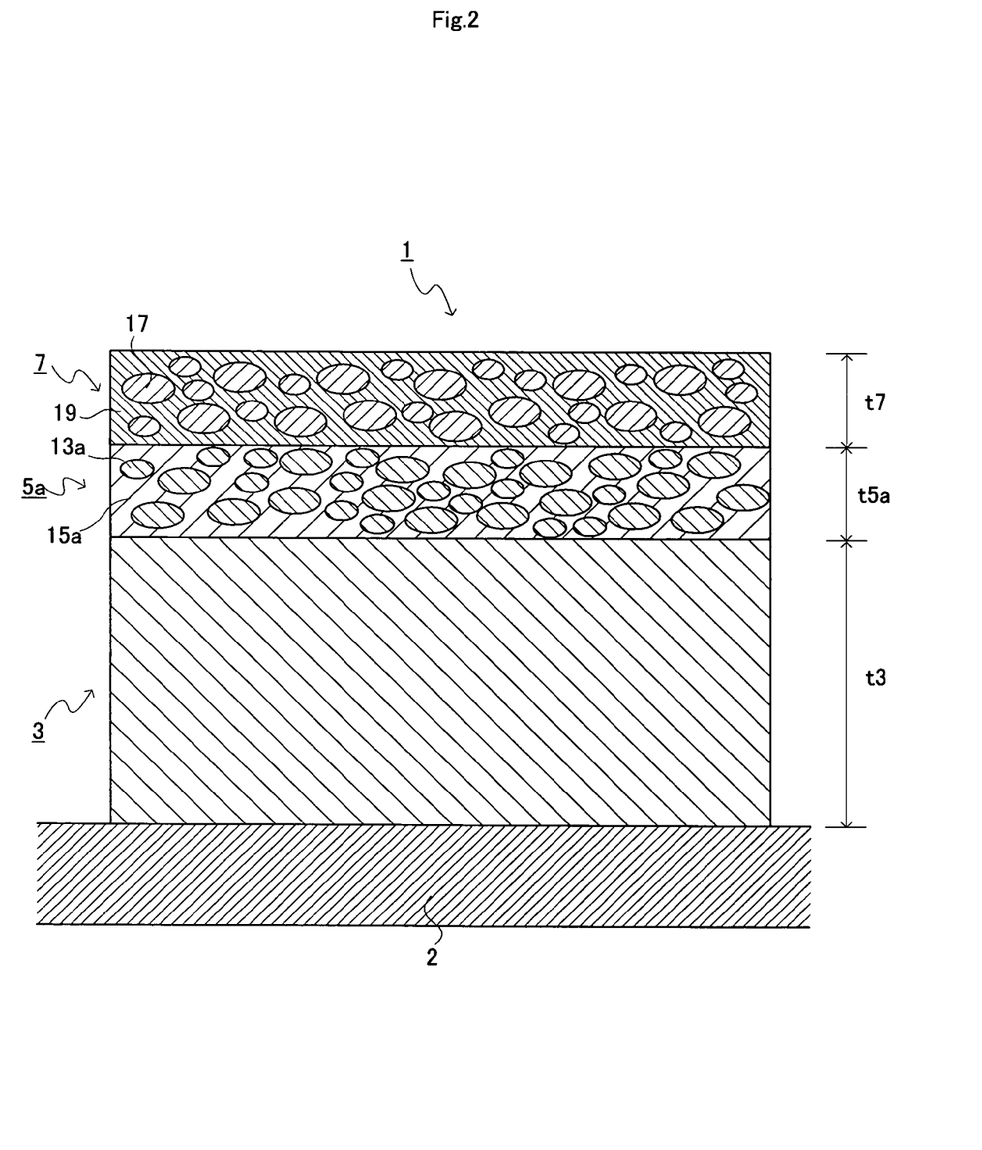
FIG. 2 is a sectional view of other example of the hydrogen sensor of the present invention.

FIG. 2 is a conceptual drawing showing other example of the hydrogen sensor of the present invention. In FIG. 2, 5a is a first protective film formed on the rare earth metal film 3 and 7 is a second protective film formed on the first protective film 5a. The first protective film 5a comprises a ceramic material 15a ($AlNx_1$) (which is a matrix) and a large number of hydrogen-permeable metal particles 13a dispersed in the matrix substantially uniformly. The diameters of the hydrogen-permeable metal particles 13a are in a range of 1 to 10 nm, preferably 2 to 6 nm and are smaller than the thickness t5a of the protective film 5a. The second protective film 7 comprises a ceramic material 19 ($AlOx_2$) (which is a matrix) and a large number of hydrogen-permeable metal particles 17 dispersed in the matrix substantially uniformly. The diameters of the hydrogen-permeable metal particles 17 are in a range of 1 to 10 nm, preferably 2 to 6 nm and are smaller than the thickness t7 of the second protective film 7. In FIG. 2, other numerals are the same as in FIG. 1.

When, as in the above, the first protective film 5a (the ceramic material: $AlNx_1$) is formed on the rare earth metal film and the second protective film 7 (the ceramic material: $AlOx_2$) is formed on the first protective film, there are the following advantages. That is, the first protective film 5a uses $AlNx_1$ of high hardness as the ceramic material and has a high protection effect to the deformation of the rare earth metal film 3. Also, the ceramic material (AlNx$_1$) used in the first protective film 5a is denatured by water vapor. However, the ceramic material (AlOx$_2$) used in the second protective film 7 is hardly denatured by water vapor and moreover intercepts water vapor. Therefore, by forming the second protective film 7 using AlOx$_2$ as the ceramic material, the denaturation of the first protective film 5a by water vapor can be prevented. Formation of the second protective film 7 containing AlOx$_2$ as the ceramic material, as the outermost layer is preferred particularly for the reason mentioned above.

Figure 3:
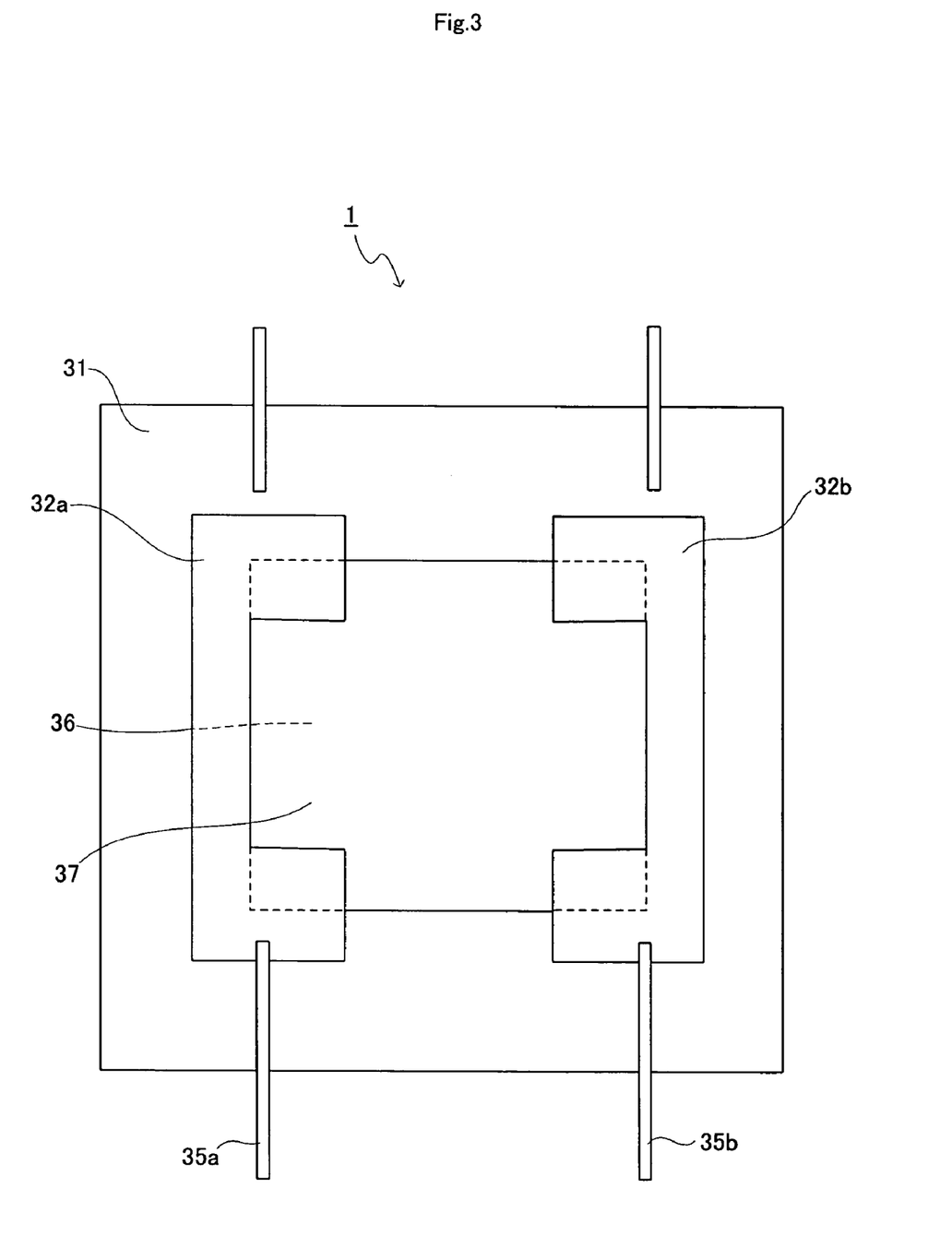
FIG. 3 is a front view of a hydrogen sensor element section into which the hydrogen sensor of the present invention has been incorporated.

FIG. 3 is a front view of a hydrogen sensor element section containing the hydrogen sensor of the present invention. In FIG. 3, 31 is a substrate. On the substrate 31 are formed a pair of element electrodes 32a and 32b so that they face each other. 35a and 35b are each a wire and are connected to the element electrodes 32a and 32b, respectively. 36 is a rare earth metal film. 37 is a protective film and is formed so as to completely cover the upper side of the rare earth metal film 36. Therefore, the rare earth metal film 36 is not shown in FIG. 3.

Figure 4:
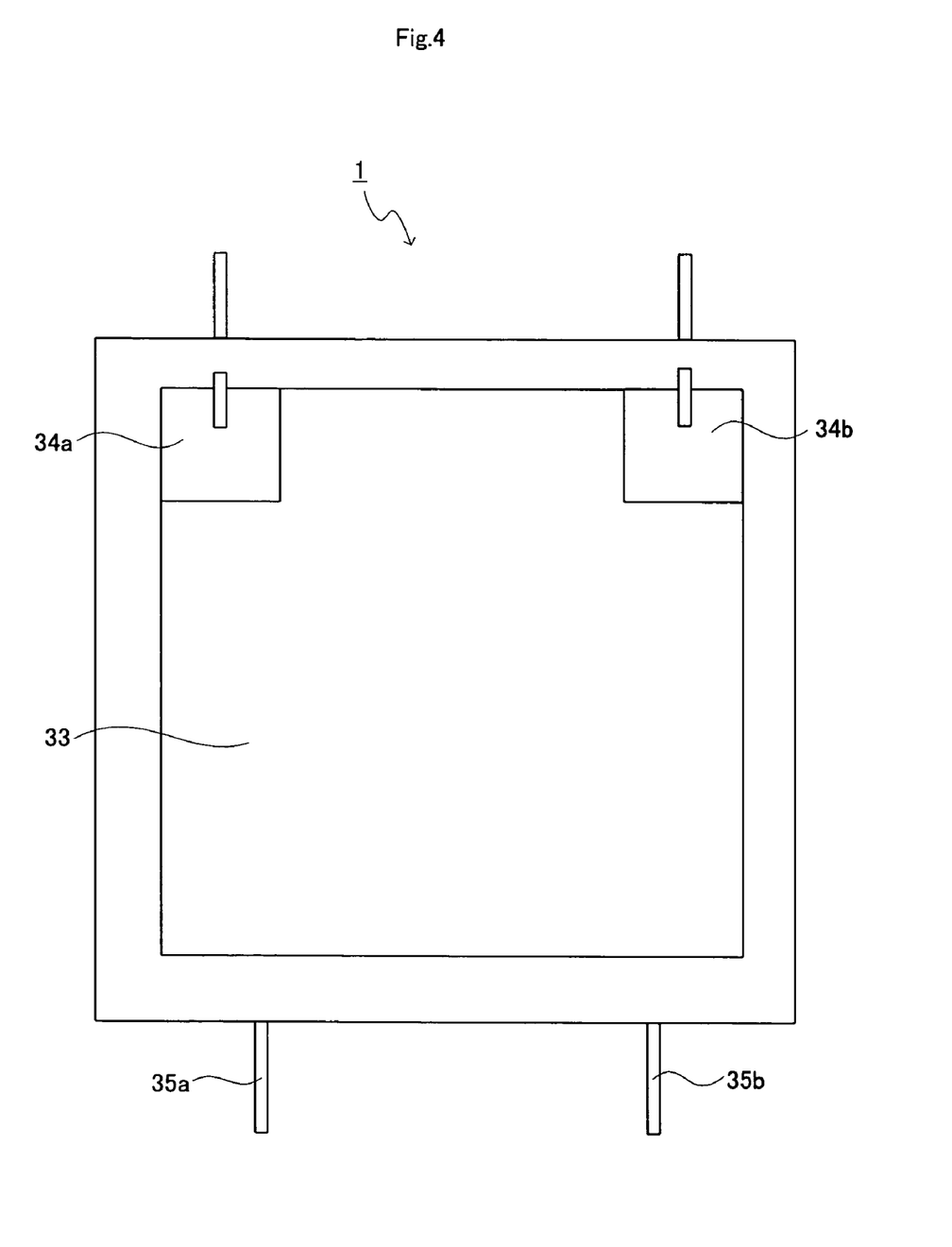
FIG. 4 is a back side view of the hydrogen sensor element section of FIG. 3.

FIG. 4 is a backside view of the hydrogen sensor section of FIG. 3. In FIG. 4, 33 is a heater made of a metal resistor, and 34a and 34b are each a heater electrode and connected to the heater 33.

Figure 5:
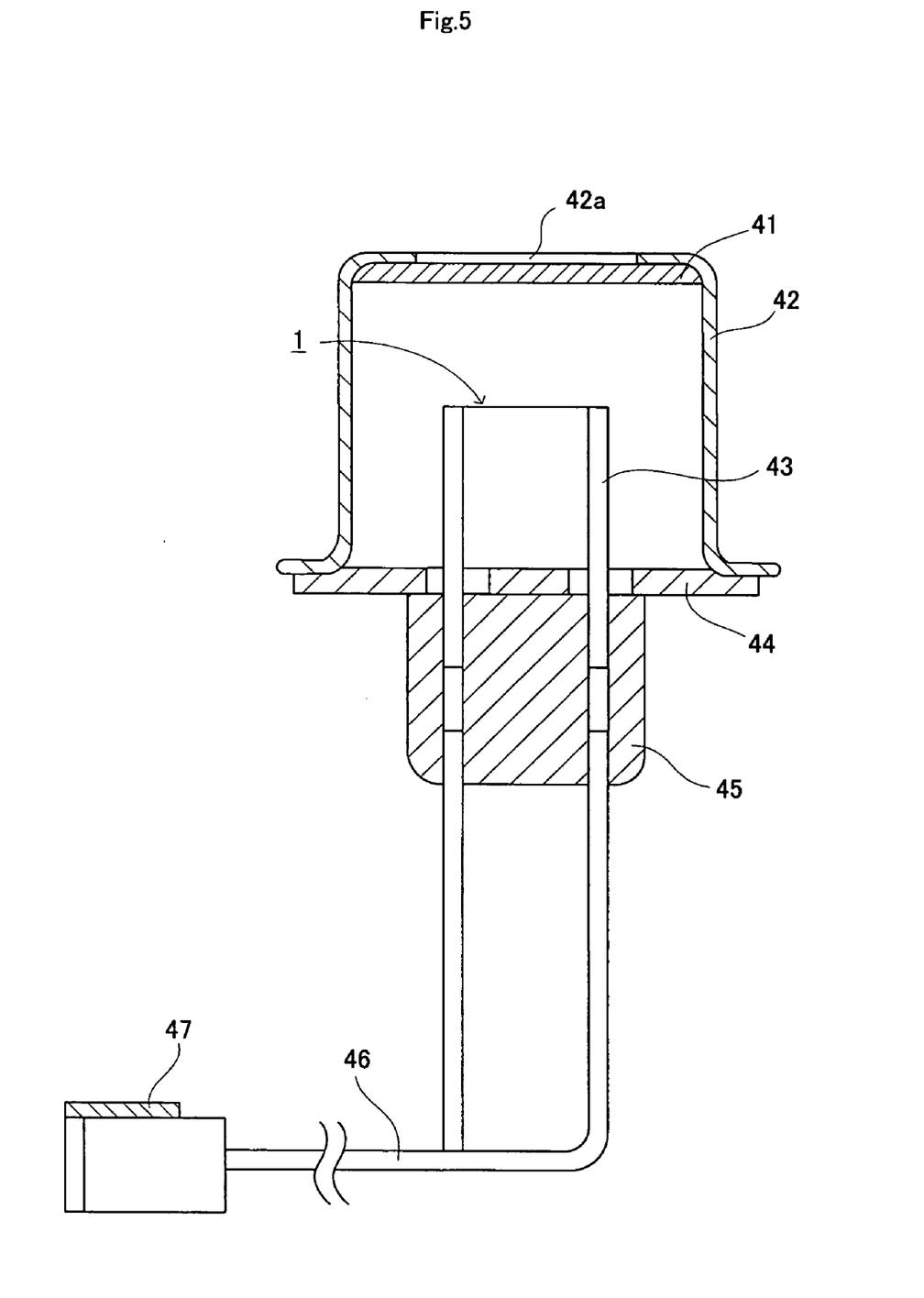
FIG. 5 is a sectional view of a sensor unit into which the hydrogen sensor of the present invention has been incorporated.

FIG. 5 is a sectional view of a sensor unit into which the hydrogen sensor of the present invention has been incorporated. In FIG. 5, 41 is a filter through which hydrogen passes; 42 is a cap; 42a is a gas passage formed in the cap 42; 43 is a pin; 44 is a plate; 45 is a grommet; 46 is a cord; and 47 is a connector.

Figure 6:
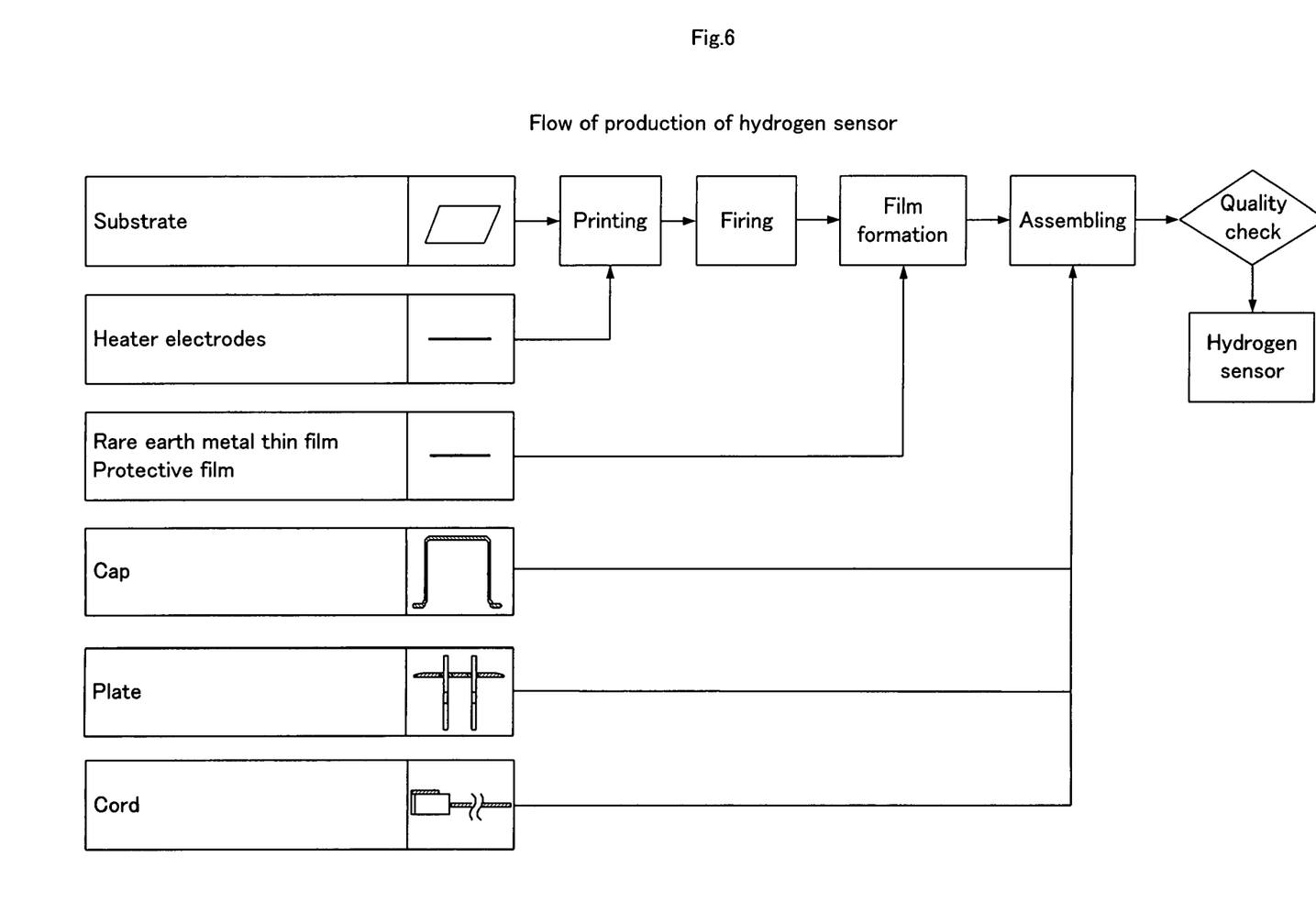
FIG. 6 is a chart showing an example of the flow of production of the hydrogen sensor of the present invention.

FIG. 6 is a chart showing an example of the flow of production of the hydrogen sensor of the present invention. First, a heater pattern is printed on a substrate using a resistor paste containing Platinum or the like and the pattern is fired to form a thin-film heater. Then, in order to form electrodes for heater, an electrode pattern is printed using a gold paste or the like and the pattern is fired. An electrode pattern is printed using a gold paste or the like and the pattern is fired to obtain a substrate for hydrogen sensor production. On this substrate for hydrogen sensor is formed a rare earth metal film, followed by formation of a protective film, whereby is obtained a hydrogen sensor.

The hydrogen sensor is integrated with a cap, a plate, a cord, etc., whereby is produced a hydrogen sensor unit. The hydrogen sensor unit obtained is subjected to quality check as necessary and, when there is no problem, the hydrogen sensor unit is used as a product.

Figure 9:
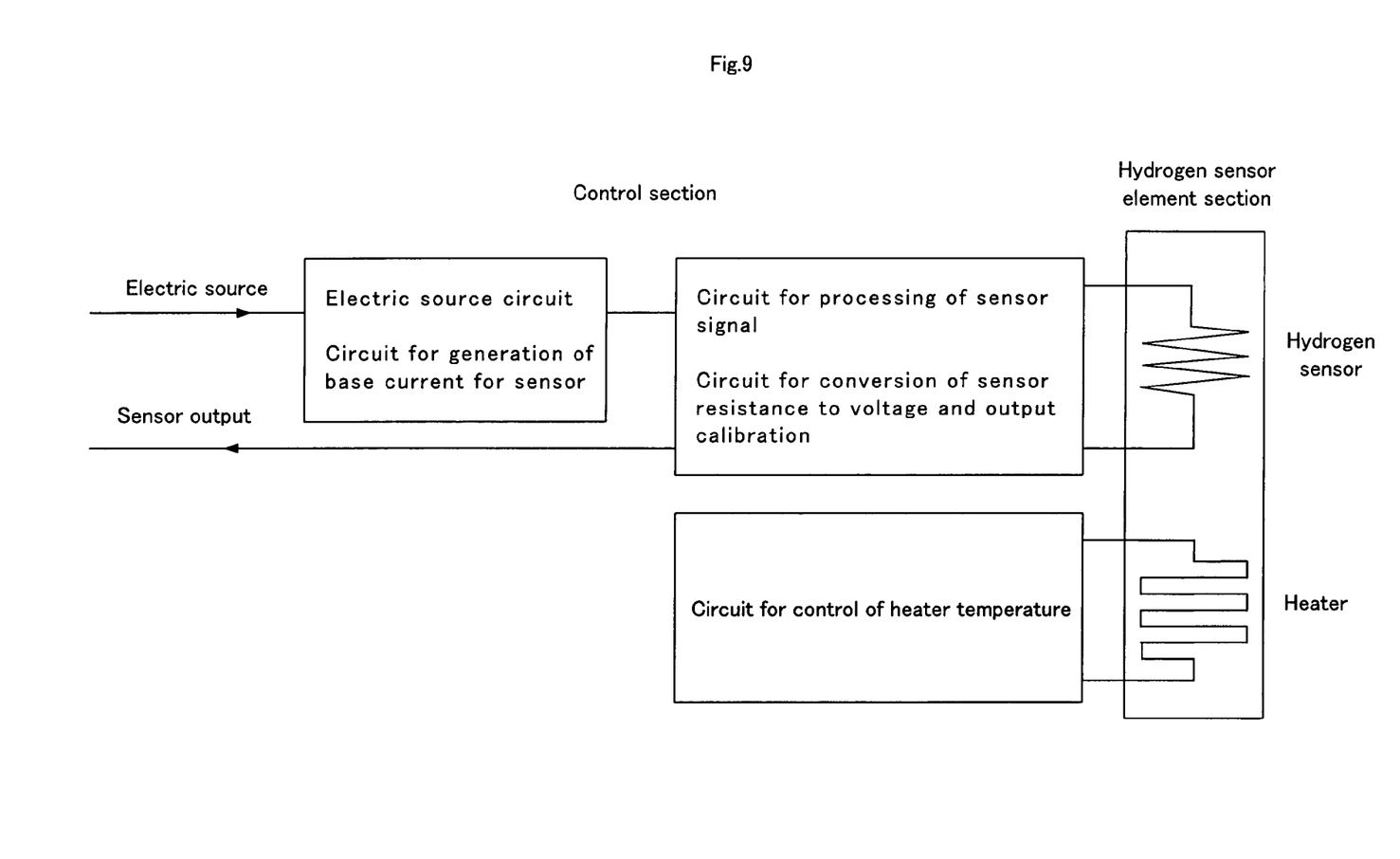
FIG. 9 is a block diagram showing an example of the control section of the hydrogen sensor of the present invention, for controlling the signal and heater temperature of the sensor.

FIG. 9 is a block diagram showing an example of the control section of the hydrogen sensor of the present invention, for controlling the signal and heater temperature of the sensor. In the base current-generating portion of the control section, the current fed from an electric source is converted into a constant current and sent to a hydrogen sensor element section. A hydrogen sensor in the hydrogen sensor element section detects hydrogen; the change in resistance and voltage which occurs thereby, is sent to a circuit for conversion/output calibration and further is subjected to signal processing in a circuit for signal processing; thereafter, a sensor output (a measured value of hydrogen gas concentration) is taken out from the circuit for signal processing. Meanwhile, control of heater output is made in a circuit for temperature control so as to allow the hydrogen sensor to have an intended temperature.

Figure 10:
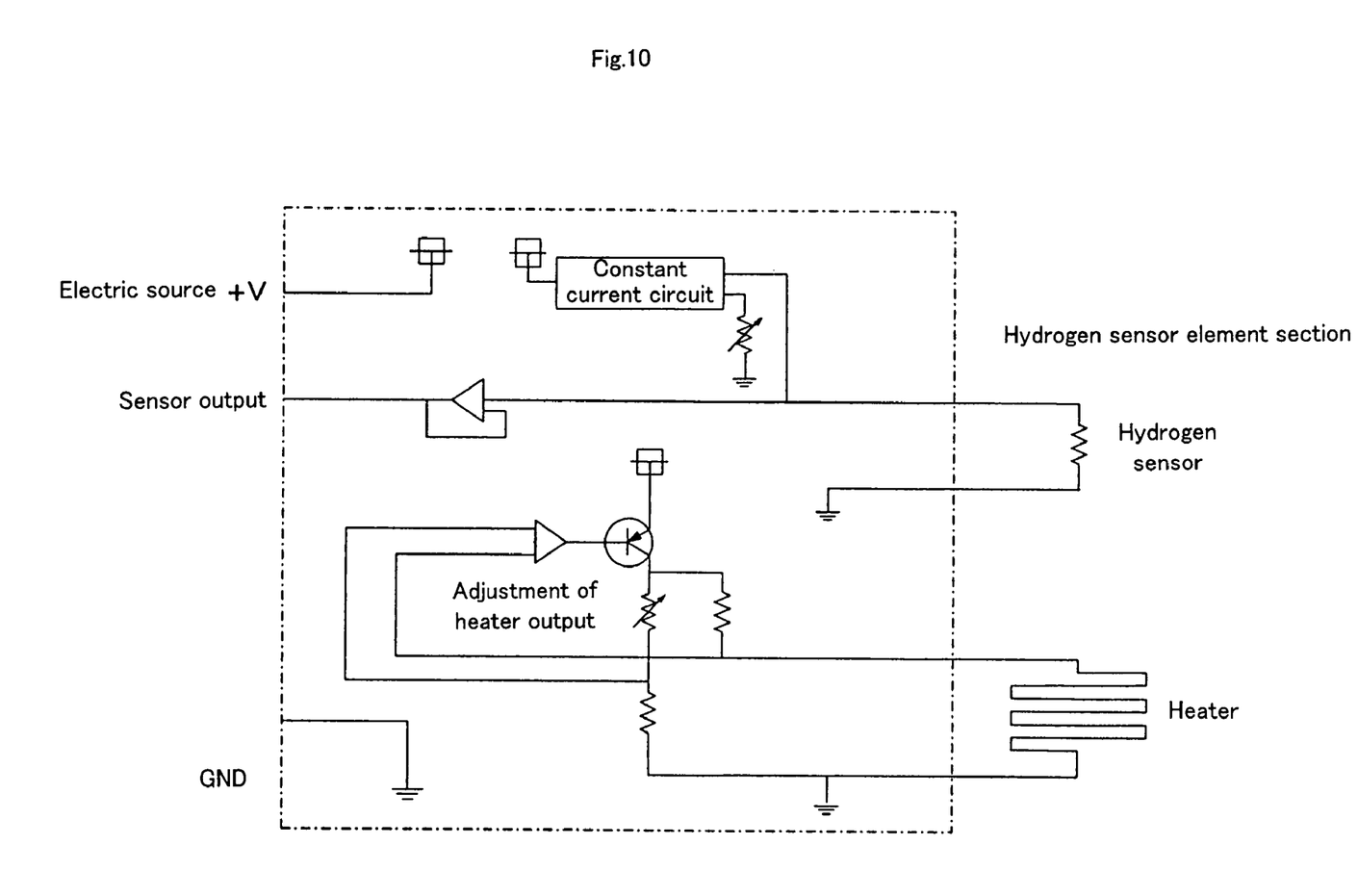
FIG. 10 is a circuit diagram showing an example of the control section of the hydrogen sensor of the present invention, for controlling the signal and heater temperature of the sensor.

FIG. 10 is a circuit diagram showing an example of the control section of the hydrogen sensor of the present invention, for controlling the signal and heater temperature of the sensor. In this circuit, the measured value of hydrogen gas concentration mentioned in FIG. 9 is taken out as a sensor output. Further, the temperature of hydrogen sensor mentioned in FIG. 9 is controlled by a circuit for adjustment of heater output.

(Rare Earth Metal Film)

The rare earth metal film 3 contains, as a main component, a rare earth metal having hydrogen detectability. The rare earth metal is preferably at least one kind selected from the group consisting of yttrium, cerium and lanthanum, for the superior hydrogen detectability. The rare earth metal film can be formed, for example, by vapor-phase growth in a vacuum atmosphere or sputtering in an argon atmosphere wherein a rare earth metal is grown or sputtered on a substrate.

The thickness of the rare earth metal film is preferably 5 to 1,000 nm. When the thickness is less than 5 nm, the rare earth metal film may have insufficient strength. Meanwhile, a thickness of more than 1,000 nm incurs a high production cost.

In the present invention, the thickness of the rare earth metal film is preferred to be determined depending upon the intended application of the hydrogen sensor to be produced. When the concentration of hydrogen gas to be measured is relatively low, for example, 1% by volume or less, particularly less than 5,000 ppm, the thickness is preferably less than 100 nm, more preferably less than 50 nm. The application in which such a low concentration of hydrogen gas is detected, includes, for example, a detector for hydrogen gas leakage. When the concentration of hydrogen gas to be measured is relatively high, for example, 1% by volume or more, particularly 5% by volume or more, the thickness is preferably 100 nm or more, particularly 300 nm or more. The application in which such a high concentration of hydrogen gas is detected, includes, for example, a hydrogen sensor for control of hydrogen gas concentration in device.

The rare earth metal film can be obtained by sputtering a rare earth metal such as yttrium or lanthanum in an argon atmosphere to form a film on a substrate.

(Protective Film)

The protective film 5 in FIG. 1 is a thin film comprising a ceramic material 15 and hydrogen-permeable metal particles 13 dispersed in the ceramic material 15. The content of the hydrogen-permeable metal particles in the protective film is preferably 30 to 70% by mass, more preferably 40 to 60% by mass. When the content is less than 30% by mass, the amount of hydrogen gas permeating through the protective film is small and the feeding of hydrogen gas to the rare earth metal film is insufficient. Meanwhile, when the content is more than 70% by mass, the deterioration of the protective film caused by the reaction of the protective film with hydrogen is striking. Also, diffusion of the hydrogen-permeable metal into the rare earth metal film is striking. As a result, the hydrogen detectability of the rare earth metal film is strikingly low.

Further, when the content of the hydrogen-permeable metal particles in the protective film is more than 70% by mass and when the thickness of the protective film is small, the protective film has a insufficient mechanical strength. Therefore, in such a case, it is difficult to produce a protective film having a thickness of 5 to 1,000 nm.

The hydrogen-permeable metal particles constituting the protective film are preferably particles of at least one kind of metal selected from the group consisting of palladium (Pd), platinum (Pt), niobium (Nb), vanadium (V) and tantalum (Ta). The hydrogen-permeable metal particles may be an alloy of the above-mentioned metal. An alloy of Pd is preferred particularly.

The hydrogen-permeable metal particles 13 may be dispersed in the ceramic material in the form of particles of single metal or particles of the above-mentioned alloy. The alloy of hydrogen-permeable metal may be an alloy used in conventional hydrogen-permeable membranes. As an element added for making the alloy, there can be mentioned, for example, calcium, iron, copper, vanadium, nickel, titanium, chromium and zirconium.

The protective film can be formed by vapor-phase growth wherein a ceramic material and a hydrogen-permeable metal are allowed to simultaneously grow in a vapor phase on the above-mentioned rare earth metal film, or by sputtering. When the ceramic material is $AlNx_1$, Al metal is used as a film-forming material and, together with a hydrogen-permeable metal, is subjected to film formation in a nitrogen gas atmosphere. When the ceramic material is $AlOx_2$, Al metal is used as a film-forming material and, together with a hydrogen-permeable metal, is subjected to film formation in an oxygen gas atmosphere. When the ceramic material is $SiNx_3$ or $SiOx_4$, film formation can be conducted in the same manner as in the case of $AlNx_1$ or $AlOx_2$, except that silicon is used in place of the Al metal.

The protective film can be formed, for example, by using a composite target (which comprises an aluminum target and a Pd chip having an area smaller than the aluminum target, mounted on the aluminum target) and sputtering the composite target in a state that a substrate is fixed above the target. Sputtering is conducted in a mixed gas atmosphere of argon and nitrogen. By this method, there can be formed, on the rare earth metal film, a protective film as a mixture (a dispersion) of Pd (a hydrogen-permeable metal) and $AlNx_1$ (a ceramic material).

The thickness of the protective film is preferably 5 to 40 nm, more preferably 7 to 20 nm. When the thickness is less than 5 nm, the harmful influence which the rare earth metal film receives from non-hydrogen gas components such as nitrogen, oxygen, ammonia, hydrocarbons and the like, may not be suppressed sufficiently. Meanwhile, when the thickness is more than 40 nm, the protective film has insufficient hydrogen permeability. As a result, the accuracy of measurement of hydrogen gas concentration may be insufficient. Or, a prolonged response time may be incurred. Further, the effect of production cost reduction is small.

Incidentally, when Pd is used as a hydrogen-permeable metal, the thickness of the protective film can be made very small because Pd is superior in separability of hydrogen gas from other gases.

The protective film may be a single layer or two or more layers. When the protective film is two or more layers, the thickness of each layer is preferably 2 to 20 nm, more preferably 4 to 15 nm. When the protective film is two or more layers, their compositions may be the same or different.

When the protective film is formed in two layers, the constitution can be, for example, $Pd+AlNx_1$ for the first layer and $Pd+AlOx_2$ for the second layer.

(Ceramic Material)

For the ceramic material 15 in FIG. 1 constituting a matrix layer in which hydrogen-permeable metal particles are dispersed, there can be used a nitride and/or an oxide of aluminum (Al) or silicon (Si), or a silicide of a rare earth metal. Of these ceramic materials, preferred are $AlNx_1$, $AlOx_2$, $SiNx_3$ and $SiOx_4$ wherein $0.5 \leq x_1 \leq 1$, $0.8 \leq x_2 \leq 1.5$, $0.7 \leq x_3 \leq 1.3$ and $1 \leq x_4 \leq 2$.

As the silicide of a rare earth metal, there can be mentioned suicides of yttrium (Y), lanthanum (La) and the like.

Of these ceramic materials, $AlNx_1$ has a high hardness and a large strength and, therefore, can effectively suppress the powdering of the hydrogen-permeable metal due to the reaction with hydrogen and is preferred particularly.

(Process for Production of Hydrogen Sensor)

The hydrogen sensor of the present invention can be produced by forming a rare earth metal film on at least one side of a substrate by vapor-phase growth or by sputtering and then forming a protective film on the rare earth metal film by vapor-phase growth or by sputtering.

As the substrate, a glass sheet, a ceramic sheet, etc. can be used. The substrate is preferably provided with a heater. The heater is preferably a thin resistor film made of platinum, ruthenium oxide, silver-palladium alloy or the like, which is formed on the substrate in a given pattern.

EXAMPLES

The present invention is described more specifically below by way of Examples. However, the present invention is in no way restricted thereto.

Example 1

Using a high-frequency magnetron sputtering apparatus, a hydrogen sensor shown in FIG. 1 was produced on a glass substrate.

First, in a high-frequency magnetron sputtering apparatus were placed a glass substrate, an yttrium target and an aluminum target having a palladium chip mounted thereon, and the pressure of the apparatus inside was reduced to about $4 \times 10^{-5}$ Pa. Then, argon gas was introduced into the apparatus and sputtering was conducted at a pressure of $9.3 \times 10^{-1}$ Pa at room temperature for 1 minute. As a result, a Y thin film (a rare earth metal film) of 30 nm in thickness was formed on the glass substrate.

Then, argon gas and nitrogen gas (volume ratio: 85/15 Pa) were introduced into the apparatus and sputtering was conducted at a pressure of $9.3 \times 10^{-1}$ Pa at room temperature for 1.5 minutes. As a result, a protective film of 10 nm in thickness was formed on the rare earth metal film, whereby a hydrogen sensor was obtained. The protective film comprises an $AlNx_1$ ($x_1=0.9$) matrix and Pd particles of 2 to 6 nm in diameter uniformly dispersed in the matrix. The Pd content in the protective film was 40% by mass.

The hydrogen sensor obtained was assembled into a hydrogen sensor unit shown in FIG. 5. Using the unit, hydrogen concentration was measured for mixed gases (mixtures of hydrogen gas and nitrogen gas) in which the hydrogen concentrations were varied in a range of 0 to 4,500 ppm. The measurement was conducted with the temperature of the hydrogen sensor kept at 70° C.

Figure 7:
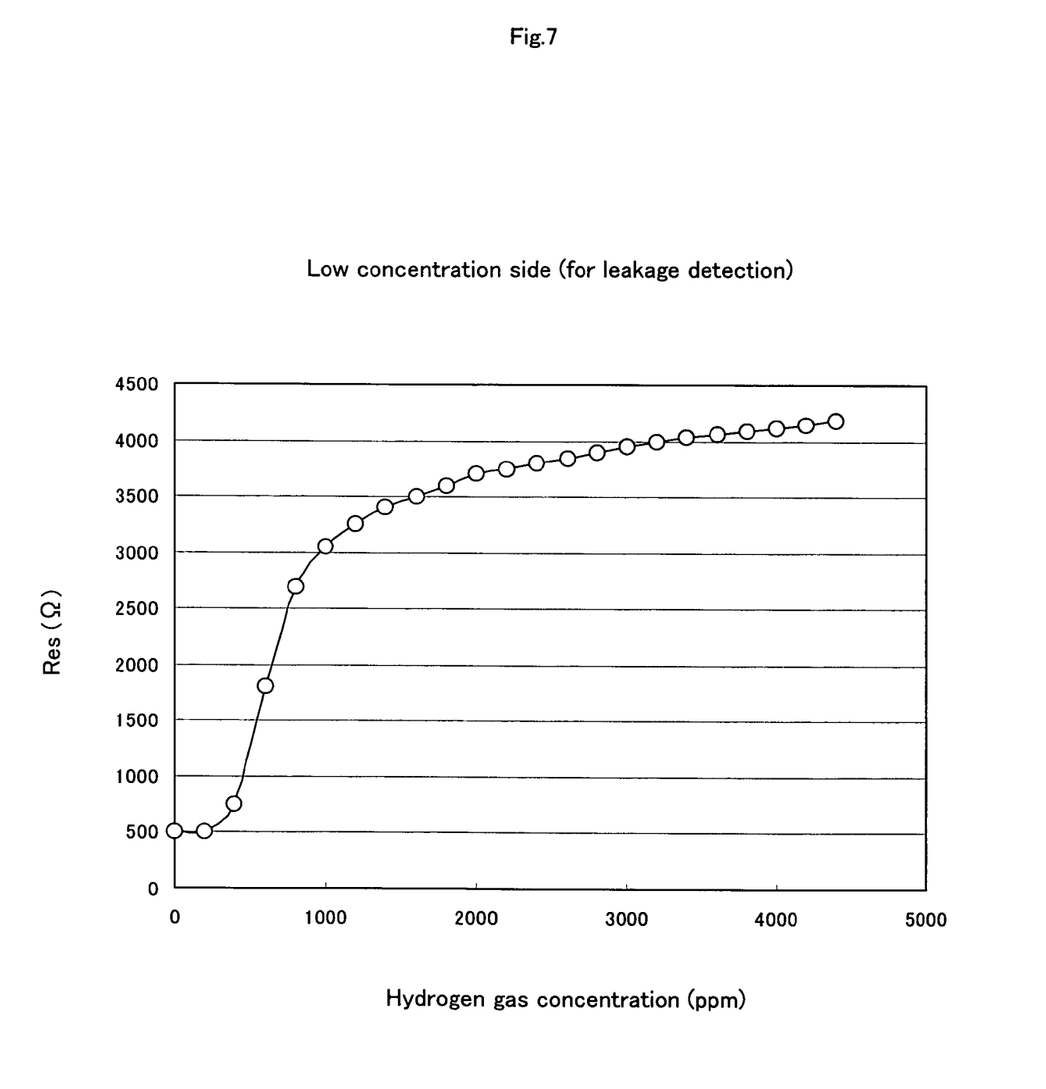
FIG. 7 is a graph showing an example of the correlation between concentration of hydrogen gas and property of rare earth metal film, in the hydrogen sensor of the present invention.

FIG. 7 is a graph showing a correlation between the hydrogen gas concentration measured using the above hydrogen sensor and the property of the rare earth metal film of the sensor. In the case of this Example, the hydrogen sensor well detected hydrogen gases of low concentrations of less than 1% (detection of hydrogen of such low concentrations is required in detection of hydrogen gas leakage).

Example 2

A hydrogen sensor of the present Example was obtained in the same operation as in Example 1 except that an yttrium thin film of 500 nm was formed, thereon was formed, as a first protective film, a thin film of 10 nm in thickness comprising an $AlNx_1$ ($x_1=0.9$) matrix and Pd articles uniformly dispersed in the matrix, and on the first protective film was formed, as a second protective film, a thin film of 10 nm in thickness comprising an $AlOx_2$ ($x_2$=1.2) matrix and Pd particles uniformly dispersed in the matrix.

Using the hydrogen sensor obtained, hydrogen gas concentrations in mixed gases (mixtures of hydrogen gas and nitrogen gas) were measured in the same operation as in Example 1 except that the hydrogen concentrations in the mixed gases were varied in a range of 2 to 100% by volume.

Figure 8:
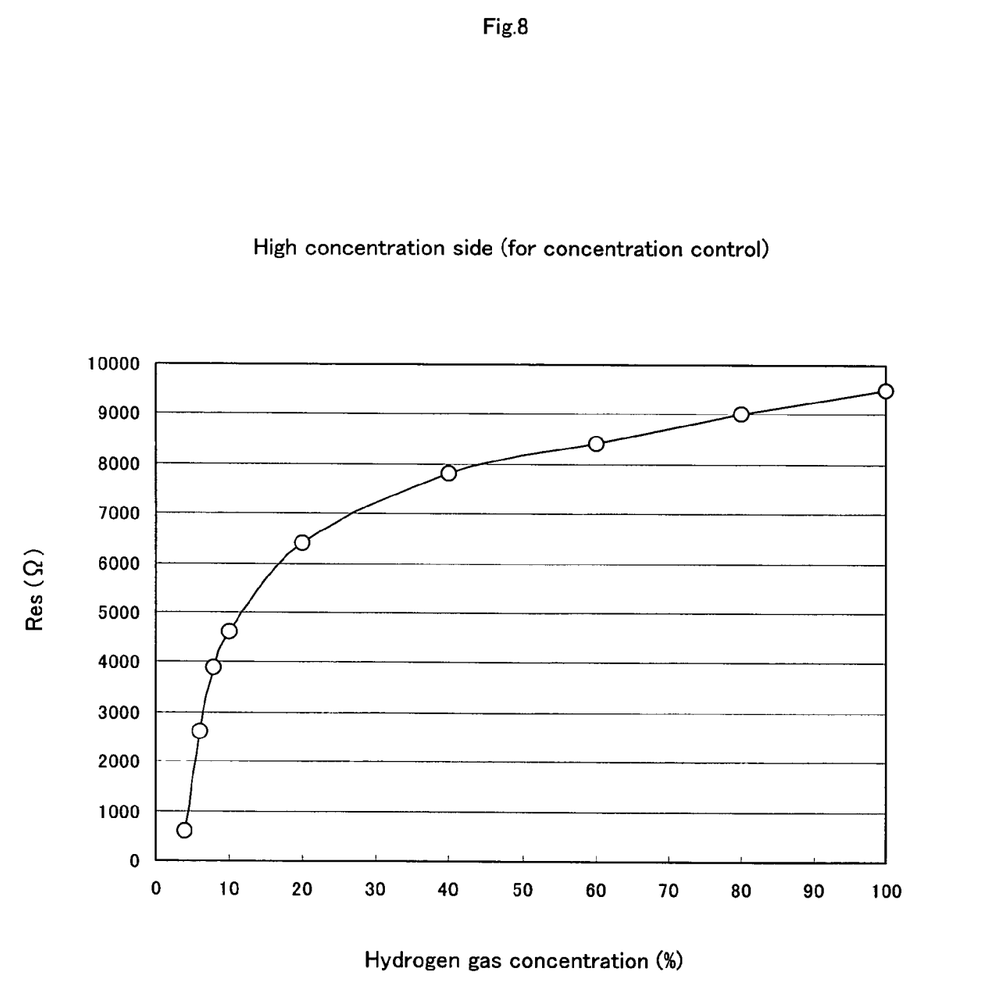
FIG. 8 is a graph showing other example of the correlation between concentration of hydrogen gas and property of rare earth metal film, in the hydrogen sensor of the present invention.

FIG. 8 is a graph showing a correlation between the hydrogen gas concentration measured using the above hydrogen sensor and the property of the rare earth metal film of the sensor. In the case of this Example, the hydrogen sensor well detected hydrogen gases of high concentrations of 1% by volume or more (measurement of hydrogen of such high concentrations is required in control of concentration of high concentration hydrogen gas).

Example 3

The hydrogen sensor of Example 2 was exposed repeatedly (10 times) to the atmosphere and then to a 100% hydrogen atmosphere at room temperature. The time in each exposure was 23.5 hours in the atmosphere and 0.5 hour in hydrogen.

The sensor output after 10 times of exposure was the same as the initial value (no change) and the surface of the protective film showed no deterioration such as crack.

Comparative Example 1

The same test as in Example 3 was conducted, using a hydrogen sensor produced in the same manner as in Example 2 except that the protective film was formed as a Pd-alone film of 10 nm in thickness. As a result, after the third exposure, there was a change in sensor output and there was no output after the fifth exposure. Further, observation of the surface of the protective film indicated cracks and partial peeling of the film.

Incidentally, the thicknesses of the rare earth metal film and the protective film were measured using a stylus profile measuring system and the compositions of these films were analyzed using an EPMA (an electron probe microanalyzer).

What is claimed is:

1. A hydrogen sensor comprising
a substrate,
a rare earth metal film formed on the substrate, and
a protective film formed on the rare earth metal film, wherein the protective film comprises a ceramic material and hydrogen-permeable metal particles dispersed in the ceramic material, the metal particles being present at 30 to 70% by mass of the protective film, and the diameters of the metal particles is 1 to 10 nm.

2. The hydrogen sensor according to claim 1, wherein the rare earth metal film has a thickness of 5 to 1,000 nm and the protective film has a thickness of 5 to 40 nm.

3. The hydrogen sensor according to claim 1, wherein the rare earth metal film is constituted by at least one kind selected from the group consisting of yttrium, cerium and lanthanum.

4. The hydrogen sensor according to claim 1, wherein the hydrogen-permeable metal particles are composed of at least one kind selected from the group consisting of palladium (Pd), platinum (Pt), niobium (Nb), vanadium (V) and tantalum (Ta).

5. The hydrogen sensor according to claim 1, wherein the ceramic material is composed of at least one kind selected from the group consisting of $AlNx_1$, $AlOx_2$, $SiNx_3$ and $SiOx_4$ wherein $0.5 \leq x_1 \leq 1$, $0.8 \leq x_2 \leq 1.5$, $0.7 \leq x_3 \leq 1.3$ and $1 \leq x_4 \leq 2$.

6. The hydrogen sensor according to claim 1, wherein the protective film is constituted by same or different two or more layers.

7. The hydrogen sensor according to claim 1, wherein the substrate is a glass sheet or a ceramic sheet.

8. The hydrogen sensor according to claim 1, wherein the substrate is provided with a heater.

9. The hydrogen sensor according to claim 8, wherein the heater is a resistor film formed on one side of the substrate, which is made of platinum, ruthenium oxide or a silver-palladium alloy.

10. The hydrogen sensor according to claim 1, wherein the rare earth metal film has a thickness of 5 to 100 nm and which is used for detection of hydrogen concentration of 1% by volume or less.

11. The hydrogen sensor according to claim 1, wherein the rare earth metal film has a thickness of 100 to 1,000 nm and which is used for detection of hydrogen concentration of 1% by volume or more.

12. A process for producing a substrate for a hydrogen sensor comprising the steps of
forming, on one side of the substrate, a rare earth metal film by vapor-phase growth or sputtering, and
forming, on the rare earth metal film, a protective film by simultaneous vapor-phase growth or sputtering of a hydrogen-permeable metal and a ceramic material, wherein the protective film comprise a ceramic material and hydrogen-permeable metal particles dispersed in the ceramic material, the metal particles being present at 30 to 70% by mass of the protective film, and the diameters of the metal particles is 1 to 10 nm.

* * * * *